(12) United States Patent
Sandrin et al.

(10) Patent No.: US 11,033,222 B2
(45) Date of Patent: Jun. 15, 2021

(54) NON-INVASIVE SYSTEM FOR CALCULATING A HUMAN OR ANIMAL, RELIABLE, STANDARDIZED AND COMPLETE SCORE

(71) Applicant: ECHOSENS, Paris (FR)

(72) Inventors: Laurent Sandrin, L'Hay les Roses (FR); Véronique Miette, Villejuif (FR); Marie Destro, Neuilly Plaisance (FR)

(73) Assignee: ECHOSENS, Paris (FR)

( * ) Notice: Subject to any disclaimer, the term of this patent is extended or adjusted under 35 U.S.C. 154(b) by 885 days.

(21) Appl. No.: 14/908,942

(22) PCT Filed: Jul. 25, 2014

(86) PCT No.: PCT/EP2014/066102
§ 371 (c)(1),
(2) Date: Jan. 29, 2016

(87) PCT Pub. No.: WO2015/014763
PCT Pub. Date: Feb. 5, 2015

(65) Prior Publication Data
US 2016/0198992 A1 Jul. 14, 2016

Related U.S. Application Data

(60) Provisional application No. 61/861,760, filed on Aug. 2, 2013.

(51) Int. Cl.
*G01N 33/00* (2006.01)
*A61B 5/00* (2006.01)
(Continued)

(52) U.S. Cl.
CPC .......... *A61B 5/4244* (2013.01); *A61B 5/4869* (2013.01); *A61B 8/485* (2013.01);
(Continued)

(58) Field of Classification Search
None
See application file for complete search history.

(56) References Cited

U.S. PATENT DOCUMENTS 7,689,437 B1 3/2010 Teller et al.
8,489,335 B2 7/2013 Cales
(Continued)

FOREIGN PATENT DOCUMENTS

CN 102302358 A 1/2012
EP 2 498 195 A1 9/2012
(Continued)

OTHER PUBLICATIONS

Castera, L.; "Invasive and non-invasive methods for the assessment of fibrosis and disease progression in chronic liver disease"; Best Practice & Research Clinical Gastroenterology 25 (2011) 291-303 (Year: 2011).*

(Continued)

*Primary Examiner* — Lori A. Clow
*Assistant Examiner* — Marie Archer
(74) *Attorney, Agent, or Firm* — Pillsbury Winthrop Shaw Pittman LLP

(57) ABSTRACT

A non-invasive system for calculating a human or animal score, the system including a measurement slave device constructed and arranged to carry out measurements of biological parameters; a measure slave device constructed and arranged to carry out measurements of physical parameters; a master device constructed and arranged to collect the biological and physical parameters and calculate the human or animal score, the score including biological and physical parameters.

16 Claims, 1 Drawing Sheet

(51) Int. Cl.
    *G01N 33/68* (2006.01)
    *C12Q 1/6883* (2018.01)
    *A61B 8/08* (2006.01)
    *G01N 33/483* (2006.01)

(52) U.S. Cl.
    CPC .......... *A61B 8/5223* (2013.01); *C12Q 1/6883* (2013.01); *G01N 33/483* (2013.01); *G01N 33/6893* (2013.01); *C12Q 2600/156* (2013.01)

(56) References Cited

U.S. PATENT DOCUMENTS

| | | | |
|---|---|---|---|
| 2005/0197680 A1 | 9/2005 | Delmain et al. | |
| 2005/0203398 A1 | 9/2005 | Sandrin et al. | |
| 2006/0031102 A1* | 2/2006 | Teller | A61B 5/411 705/3 |
| 2007/0225919 A1 | 9/2007 | Jeffrey et al. | |
| 2008/0299554 A1* | 12/2008 | Huang | C12Q 1/6883 435/6.11 |
| 2012/0186019 A1 | 7/2012 | Rawls-Meehan | |
| 2013/0079236 A1 | 3/2013 | Holmes | |
| 2014/0005500 A1* | 1/2014 | Gales | A61B 5/4842 600/301 |
| 2014/0170741 A1* | 6/2014 | Wang | A61B 5/4244 435/288.7 |

FOREIGN PATENT DOCUMENTS

| | | |
|---|---|---|
| EP | 2 600 266 A1 | 6/2013 |
| WO | WO 2010/097472 A1 | 9/2010 |

OTHER PUBLICATIONS

Maklad, N. F. et al; "Attenuation of Ultrasound in Normal Liver and Diffuse Liver Disease In Vivo"; Ultrasonic Imaging 6, (1984); 117-125 (Year: 1984).*

Sasso, M. et al; "The controlled attenuation parameter (CAP): A novel tool for the non-invasive evaluation of steatosis using Fibroscan®"; Clinics and Research in Hepatology and Gastroenterology (2012) 36, 13-20 (Year: 2012).*

Kim, S. U. et al; "The usefulness of liver stiffness measurement using FibroScan in chronic hepatitis C in South Korea: A multicenter, prospective study"; Journal of Gastroenterology and Hepatology 26 (2011) 171-178 (Year: 2011).*

Sasso, M. et al; "Controlled Attenuation Parameter (CAP): A novel VCT guided ultrasonic attenuation measurement for the evaluation of hepatic steatosis"; Ultrasound in Med. & Biol., vol. 36, No. 11, pp. 1825-1835, 2010 (Year: 2010).*

Sandrin, L. et al; "Transient Elastography: A new noninvasive method for assessment of hepatic fibrosis"; Ultrasound in Med & Biol, vol. 29, No. 12, pp. 1705-1713, 2003 (Year: 2003).*

Chan, H. L.; "Alanine aminoransferase-based algorithms of liver stiffness measurement by transient elastography (Fibroscan) for liver fibrosis in chronic hepatitis B"; Journal of Viral Hepatitis, 2009, 16, 36-44. (Year: 2009).*

Tapper, E. B. et al.; "Levels of Alanine Aminotransferase Confound Use of Transient Elastography to Diagnose Fibrosis in Patients With Chronic Hepatitis C Virus Infection"; Clinical Gastroenterology and Hepatology (2012) 10:932-937. (Year: 2012).*

International Search Report as issued in International Patent Application No. PCT/EP2014/066102, dated Mar. 27, 2015.

Friedrich-Rust, M., et al., "Real-Time Elastography for Noninvasive Assessment for Liver Fibrosis in Chronic Viral Hepatitis," Hepatobiliary Imaging, American Journal of Roentgenology, American Roentgen Ray Society, vol. 188, No. 3, Mar. 2007, pp. 758-764.

Calès, P., et al., "Accuracy of liver fibrosis classifications provided by non-invasive tests," universite angers, Apr. 2010, Retrieved from the Internet <http://www.biols.fr/uploads/rte/File/EASL2010P1046(1).pdf>, pp. 1-2.

Boursier, J., et al., "A new fibrosis staging method provides very accurate noninvasive diagnosis of liver fibrosis without liver biopsy," universite angers, Apr. 2010, Retrieved from the Internet <http://www.biols.fr/uploads/rte/File/EASL2010P1046(1).pdf>, pp. 1-2.

Office Action as issued in Russian Patent Application No. 2016107170, dated Sep. 24, 2018.

* cited by examiner

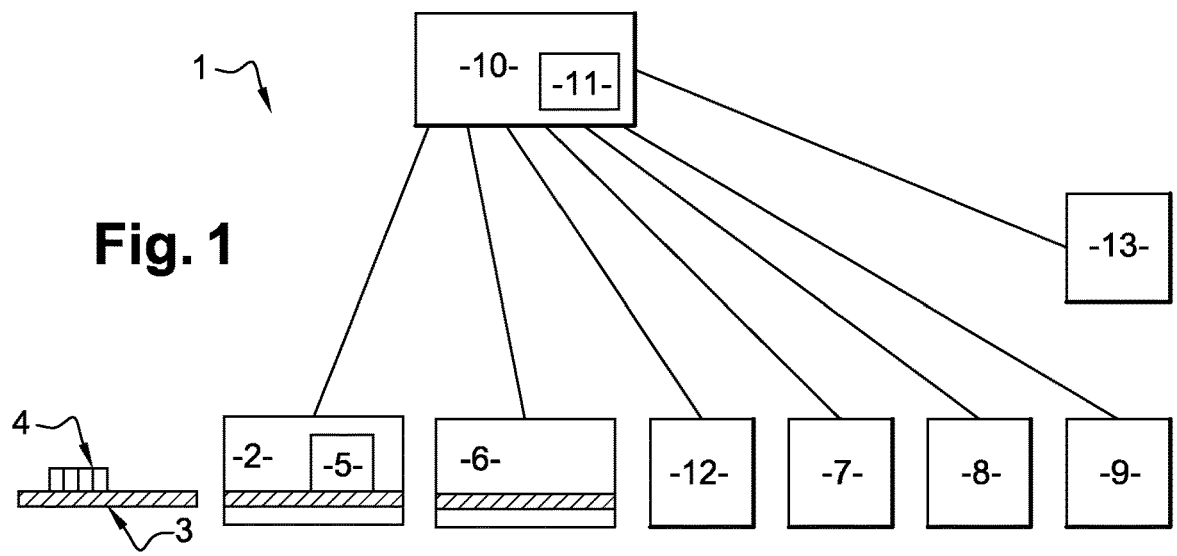
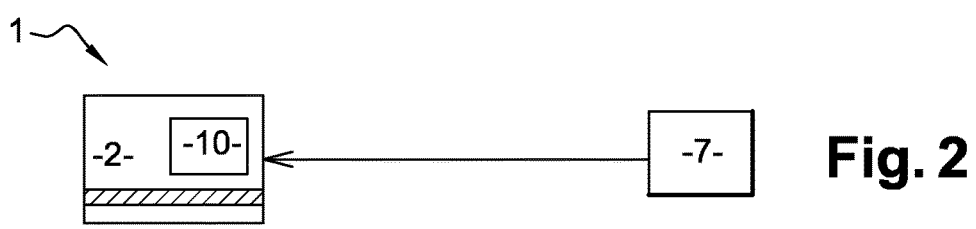
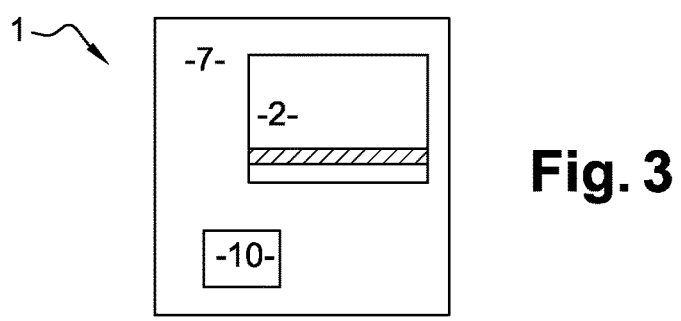
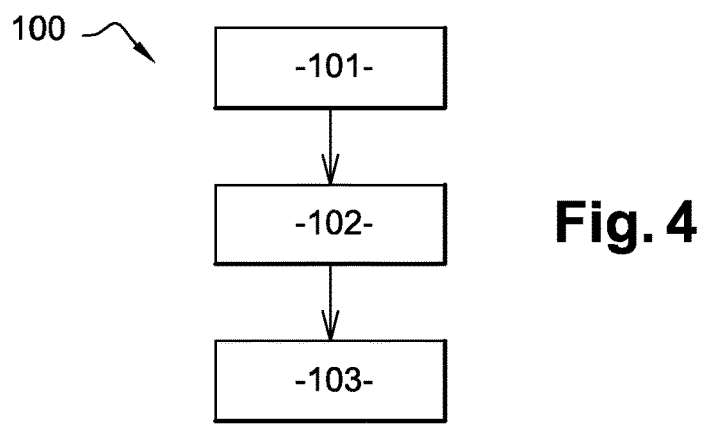

NON-INVASIVE SYSTEM FOR CALCULATING A HUMAN OR ANIMAL, RELIABLE, STANDARDIZED AND COMPLETE SCORE

CROSS-REFERENCE TO RELATED APPLICATIONS

This is the U.S. National Stage of PCT/EP2014/066102, filed Jul. 25, 2014, which in turn claims priority to U.S. patent application Ser. No. 61/861,760, filed Aug. 2, 2013, the entire contents of all applications are incorporated herein by reference in their entireties.

FIELD

The present invention relates generally to a non-invasive system arranged and construed to calculate a human or animal accurate, reliable, standardized and complete score.

BACKGROUND

Many different blood tests have been designed to diagnose Fibrosis or Cirrhosis in Patients with Chronic Hepatitis C Virus Infection (HEPASCORE® (a biochemical severity scoring system based on liver function tests in predicting the extent of liver fibrosis/cirrhosis in patients with hepatitis C infection), APRI (AST (aspartate aminotransferase) to Platelet Ratio Index (APRI) is an index that determines the likelihood of hepatic fibrosis and cirrhosis in patients with hepatitis C), ELF (The Enhanced Liver Fibrosis (ELF) score is an ECM marker set consisting of tissue inhibitor of metalloproteinases 1 (TIMP-1), amino-terminal propeptide of type III procollagen (PIIINP) and hyaluronic acid (HA) showing good correlations with fibrosis stages in chronic liver disease), FIB-4 (The Fibrosis 4 score (FIB-4 is a non-invasive scoring system based on several laboratory tests that help to estimate the amount of scarring in the liver), FIBROINDEX (index for predicting significant fibrosis in patients with chronic hepatitis C), FIBROTEST® (a biomarker test that uses the results of six blood serum tests to generate a score that is correlated with the degree of liver damage in people with a variety of liver diseases), FIBROSURE® (a blood test that measures liver fibrosis and inflammation), FIBROMETER (a blood test used to aid in the evaluation and management of liver fibrosis), etc. The publication "Blood Tests to Diagnose Fibrosis or Cirrhosis in Patients With Chronic Hepatitis C Virus Infection, Annals of Internal Medicine, Jun. 4, 2013" disclose such blood tests. All of these are trademark registered). These blood tests may be based on serum markers, general blood parameters (hematology, biochemistry) associated with demographic information and personal parameters such as weigh, height, etc.

Systems for photometric analysis for determining the concentration of a substance carried by a blood sample or other fluid sample taken from a human or an animal are well known in the art. Such systems generally proceed to blood fractionation by centrifugation. They can work on blood serum, other on whole blood. Different reagents may be added to the biological fluid to be analyzed.

The systems generally comprise a light source and a light detector disposed to detect light directed through the sample containing the biological fluid-reagent mixes. This light is partially absorbed by the products of reactions between the reagents and components of blood sample. The degree to which light is absorbed is dependent upon the concentration of the reaction product in the blood sample. By comparing the intensity of the light transmitted through the sample with a reference intensity, the concentration of a given component of the reaction between the blood sample and the reagent can be determined. The concentration of the reaction is then used to calculate the concentration of a corresponding biochemical parameter in the blood sample.

In summary, such system allows the rapid centrifugation, analysis, and measurement of biochemical parameter present in fluids including blood or other body fluid samples.

However, these blood tests suffer from strong limitations as blood parameters are only indirect markers of liver health status. Furthermore, the results may vary from one laboratory to another depending on the systems used to measure blood parameter, the nature of the reagents used and the travel time of the blood sample from the blood collection place to the laboratory. These differences obviously affect the performances of mathematical formulae involving several biomarkers quantities.

For the foregoing reasons, the measurement of components present in fluids does not permit obtaining a reliable, accurate, standardized and complete score.

Other biomarkers can be used to assess liver diseases. As an example, a physical biomarker, liver stiffness measured by Vibration-Controlled Transient Elastography, has been shown to be very well correlated to liver fibrosis in patients with chronic liver diseases. The publications "Liver stiffness: a novel parameter for the diagnosis of liver disease, Hepatic Medicine: Evidence and Research 2010; 2" and "Transient elastography: a new noninvasive method for assessment of hepatic fibrosis; ultrasound in Medicine and Biology, Volume 29, Number 12, 2003" discloses such correlation. However liver stiffness is influenced by other factors such as inflammation and congestion. Interestingly liver inflammation can be assessed by elevated levels of liver enzymes in blood.

SUMMARY

An aspect of the invention is directed to a system and a method that overcome the aforementioned drawbacks. Accordingly, an embodiment of the invention is directed to a non-invasive system constructed and arranged to calculate a human or animal accurate, reliable, standardized and complete score.

To achieve this, an aspect of the present invention is directed to a non-invasive system for calculating a human or animal score, the system comprising:
- a measurement slave device constructed and arranged to carry out measurements of biological parameters;
- a measurement slave device constructed and arranged to carry out measurements of physical parameters;
- a master device constructed and arranged to collect the biological and physical parameters and calculate the human or animal score, the score comprising biological and physical parameters.

As the calculated score takes into account quantitative biological parameters and quantitative physical parameters, the calculated score is accurate, reliable, standardized and complete.

In a non limiting embodiment, the measurement slave device constructed and arranged to carry out measurements of biological parameters is an in-vitro measurement slave device.

In a non limiting embodiment, the measurement slave device constructed and arranged to carry out measurements of physical parameters is an in-vivo measurement slave device.

In a non limiting embodiment, the in-vitro measurement slave device is a clinical chemistry analyzer.

In a non limiting embodiment, the clinical chemistry analyzer is constructed and arranged to measure biochemical parameters selected from the group consisting of: albumin, alkaline phosphastase, aspartate aminotransferase, alanine aminotransferase, amylase, bilirubin, blood urea nitrogen, calcium, creatine kinase, chloride, creatinine, C-reactive protein, gamma glutamyl, transpeptidase, glucose, potassium, magnesium, sodium, phosphorus, total carbon dioxide, total protein, uric acid, total cholesterol, high density lipoprotein, triglycerides, hyaluronic acid, alpha 2 macroglobulin, or any combination thereof.

In a non limiting embodiment, the clinical chemistry analyzer is constructed and arranged to measure biochemical parameters selected from the group consisting of: aspartate aminotransferase, hyaluronic acid, alanine aminotransferase, bilirubin, alpha 2 macroglobulin, gamma glutamyl transpeptidase or any combination thereof.

In a non limiting embodiment, the in-vitro measurement slave device is a clinical hematology analyser.

In a non limiting embodiment, the clinical hematology analyzer is constructed and arranged to measure hematology parameters selected from the group consisting of: platelet, white blood cell, red blood cell, prothrombin index, and INR, or any combination thereof.

In a non limiting embodiment, the hematology analyser is constructed and arranged to measure hematology parameters selected from the group consisting of: platelet, prothrombin index, and INR, or any combination thereof.

In a non limiting embodiment, the in-vitro measurement slave device is a DNA-based test analyzer.

In a non limiting embodiment, the DNA-based test analyzer is constructed and arranged to measure genetic maker selected from the group consisting of IL28, AZIN1, TLR4, and TRPM5, or any combination thereof.

In a not limited embodiment, the in-vitro measurement slave device is an immunology-based test analyzer.

In a not limited embodiment, the immunology-based test analyzer is constructed and arranged to measure protein maker selected from the group consisting of Albumin, Bilirubin, CRP, Ferritin, Alpha 2 macroglobulin, Hyaluronic acid, Laminin, Apolipoprotein A1, Haptoglobin, PIIINP, TIMP-1, MMPs, Adiponectin, IL-6, Alpha Fetoprotein, CK18, Chemokine ligand 2, TNF alpha, HbA1c, anti-HCV, HBsAg, HBsAb, HbeAg, HbeAb, and HbcAb, or any combination thereof.

In a non limiting embodiment, the in-vivo measurement slave device is an elastography device.

In a non limiting embodiment, the elastography device is constructed and arranged to measure parameters of the liver from the group consisting of: elasticity, stiffness, viscosity, ultrasound attenuation, and shear wave speed, or any combination thereof.

In a non limiting embodiment, the in-vivo measurement slave device is a body composition analyzer.

In a non limiting embodiment, the body composition analyzer is constructed and arranged to measure parameters from the group consisting of: body weight, body fat content, or any combination thereof.

In a non limiting embodiment, the non-invasive system comprises a master device constructed and arranged to collect personal and demographical parameters, the master device being constructed and arranged to collect the personal and demographic parameters and calculate the score, the score comprising personal and/or demographic parameters.

In a non limiting embodiment, the master device is a server.

In a non limiting embodiment, the master device is located in a slave device.

An embodiment of the invention relates also to a human or animal score combining physical parameters and biological parameters,
the biological parameters being selecting from the group consisting of: albumin, alkaline phosphastase, aspartate aminotransferase, alanine aminotransferase, amylase, bilirubin, blood urea nitrogen, calcium, creatine kinase, chloride, creatinine, C-reactive protein, gamma glutamyl, transpeptidase, glucose, potassium, magnesium, sodium, phosphorus, total carbon dioxide, total protein, uric acid, total cholesterol, high density lipoprotein, triglycerides, hyaluronic acid, alpha 2 macroglobulin platelet, white blood cell, red blood cell, prothrombin index, INR, IL28, AZIN1, TLR4, and TRPM5, Ferritin, Laminin, Apolipoprotein A1, Haptoglobin, PIIINP, TIMP-1, MMPs, Adiponectin, IL-6, Alpha Fetoprotein, CK18, Chemokine ligand 2, TNF alpha, HbA1c, anti-HCV, HBsAg, HBsAb, HbeAg, HbeAb, and HbcAb or any combination thereof,
the physical parameters being selecting from the group consisting of: elasticity, stiffness, viscosity, ultrasound attenuation, shear wave speed, height, and weight or any combination thereof.

In a non limiting embodiment, the human or animal score combines furthermore personal and/or demographic parameters.

An embodiment of the invention relates also to a disposable device that contains reagents which are constructed and arranged to react with a biological sample taken from a human or an animal, the disposable device being constructed and arranged to be loaded into a slave device constructed and arranged to carry out measurements of biological parameters; the disposable device comprising a device configured to identify the human or animal score according to an embodiment of the invention.

An embodiment of the invention relates also to a non-invasive method for calculating a human or animal score, the method comprising:
in the vicinity of a patient, measuring and calculating biological parameters;
in the vicinity of a patient, measuring and calculating physical parameters;
determining the human or animal score comprising the biological and physical parameters measured and calculated.

BRIEF DESCRIPTION OF THE DRAWINGS

The accompanying drawings are included to provide a further understanding of the invention and are incorporated in and constitute a part of this specification, to illustrate embodiments of the invention and, together with the description, to explain the principles of the invention:

FIG. 1 represents a non-invasive system for calculating an accurate, reliable, standardized and complete human or animal score according to an embodiment of the invention;

FIG. 2 depicts a non-invasive system for calculating an accurate, reliable, standardized and complete human or animal score according to another embodiment of the invention; and FIG. 3 illustrates a non-invasive system for calculating an accurate, reliable, standardized and complete human or animal score according to another embodiment of the invention, FIG. 4 illustrates a non-invasive method for calculating a human or animal score.

DESCRIPTION OF SPECIFIC EMBODIMENTS

In reference to FIG. 1, a non-invasive system 1 for calculating a human or animal accurate, reliable, standardized and complete score according to an embodiment of the invention is represented. In a non limiting embodiment, this score may be dedicated to the field of hepatology and more particularly may be related to the liver.

The non-invasive system 1 comprises a first measurement slave device 2 constructed and arranged to carry out measurements of biological parameters. In a non limiting embodiment, the first measurement slave device 2 is an in-vitro measurement slave device.

The first in-vitro measurement slave device 2 may be a point of care testing, also known under the acronym POCT. This point of care testing is near or at the site of patient examination and eliminates the time consuming need to send and carry a biological sample to a central laboratory for testing. Therefore, the point of care testing allows a user or a medical practitioner at the patient's location, to obtain a reliable, accurate quantitative, analytical result that is qualitatively better as compared to a result which would be obtained in a laboratory due to the fact that the biological sample is not transported to the laboratory (i.e. at a different location than the patient's location).

In a non limiting embodiment, the first in-vitro measurement slave device 2 is a POCT which may be a system for photometric analysis for determining the concentration of a substance carried by a blood sample or other fluid sample taken from a human or an animal. Such system comprises a disposable device 3 having a plurality of cuvettes containing reagents wherein, for instance, a blood sample drawn from a human is placed. The reagents are constructed and arranged to react with the blood sample. The disposable device 3 is adapted to be loaded into the first in-vitro measurement slave device 2. In a non limiting embodiment, the disposable device 3 comprises a device 4 configured to identify the parameters to be measured, the device 4 being formed by a barcode. In this embodiment, the first in-vitro measurement measurement slave device 2 formed by a point of care testing comprises a scanner 5 to scan the barcode 4 to identify the parameters to be measured.

Then, when the disposable device 3 is loaded into the first in-vitro measurement slave device 2 and the parameters to be measured are identified, the first in-vitro measurement slave device 2 centrifuges the blood sample by a rotation of the disposable device 3 in order to separate the blood plasma from the blood's cellular components. The first in-vitro measurement slave device 2 further comprises a light source and a light detector arranged to detect light directed through the cuvettes containing the biological fluid-reagent mixes. The light is partially absorbed by the products of the reactions between the reagents and components of the blood sample. The degree to which the light is absorbed is dependent upon the concentration of the reaction product in the blood sample. By comparing the intensity of the light transmitted through the cuvette with a reference intensity, the concentration of a given product of the reaction between the fluid and the reagent can be determined. The concentration of the reaction product is then used to calculate the concentration of corresponding biological parameters in the blood sample. In this example, the POCT is a clinical chemistry analyzer. The disposable device may be a rotor for example.

According to various embodiments of the invention, the clinical chemistry analyzer 2 is adapted to measure biochemical parameters selected from the group consisting of albumin, alkaline phosphastase, aspartate aminotransferase, alanine aminotransferase, amylase, bilirubin, blood urea nitrogen, calcium, creatine kinase, chloride, creatinine, C-reactive protein, gamma glutamyl, transpeptidase, glucose, potassium, magnesium, sodium, phosphorus, total carbon dioxide, total protein, uric acid, total cholesterol, high density lipoprotein, triglycerides, hyaluronic acid, and alpha 2 macroglobulin, or any combination thereof.

In the example illustrated in FIG. 1, the non-invasive system 1 comprises a second in-vitro measurement slave device 6 constructed and arranged to carry out measurements of biological parameters. The second in-vitro measurement slave device 6 may be a point of care testing (POCT). In this example, the POCT corresponding to the second in-vitro measurement slave device 6 is a clinical hematology analyzer. According to the non limiting embodiment of the invention, the clinical hematology analyzer is adapted to measure hematology parameters selected from the group consisting of platelet, white blood cell, red blood cell, prothrombin index, and INR, or any combination thereof.

In a non limiting embodiment illustrated in FIG. 1, the non-invasive system 1 comprises a third in-vitro measurement slave device 12 constructed and arranged to carry out measurements of genetic makers. The third in-vitro measurement slave device 12 may be a DNA-based test analyzer which may be a system for DNA microarray (or DNA chip) for determining gene expression and SNPs (Single Polymorphism Nucleotide) from a drop of blood or other biofluid sample taken from a human or an animal.

For example, such system comprises a plastic disposable chip (or disposable device) containing compartments with a reaction mix adapted to be loaded into a portable lab. The portable lab includes a heating device, a laser, a CCD based detector and an on-board control system. Each compartments of the disposable device perform a single DNA-based diagnostic test including all components required for the reaction such as DNA sequence used for hybridation and fluorescent marker.

When the disposable device is loaded into the portable lab, sample is prepared; DNA is extracted then amplified by PCR (Polymerase Chain reaction), purified and reading is done.

According to an embodiment of the invention, analysis could be performed on any potential genetic marker of liver disease such as IL28, AZIN1, TLR4, TRPM5.

In a not limited embodiment illustrated in FIG. 1, the non-invasive system 1 comprises a fourth in-vitro measurement slave device 13 constructed and arranged to carry out measures of immunologic markers. The fourth in-vitro measure slave device 13 may be a multiplexed magnetic assay which can quantify immunologic parameters from a drop of blood or other bio-fluid sample taken from a human or an animal. According to embodiments of the invention, analysis could be performed on any immunologic markers related to liver disease such as Albumin, Bilirubin, CRP, Ferritin, Alpha 2 macroglobulin, Hyaluronic acid, Laminin, Apolipoprotein A1, Haptoglobin, PIIINP, TIMP-1, MMPs, Adiponectin, IL-6, Alpha Fetoprotein, CK18, Chemokine ligand 2, TNF alpha, HbA1c, anti-HCV, HBsAg, HBsAb, HbeAg, HbeAb, and HbcAb or any combination thereof.

In the example illustrated in FIG. 1, the non-invasive system 1 comprises also a first measurement slave device constructed and arranged to carry out measurements of physical parameters. In a non limiting embodiment, the first measurement slave device is a first in-vivo measurement slave device 2. The first in-vivo measurement slave device constructed and arranged to carry out measurements of physical parameters may be an elastography device 7 or an ultrasound scanner. Such elastography device 7 generally comprises an ultrasonic transducer, a position sensor, a controlled electrodynamic actuator connected to the ultrasonic transducer. Such elastography device 7 is, for instance, disclosed by document US20050203398 and incorporated herein by reference in its entirety. Such elastography device 7 is constructed and arranged to emit and acquire ultrasonic signals to follow tissue motions associated with shear wave propagation through biological tissues. The so called shear waves are induced by natural body motion (breathing, heart beats, etc), by mechanical actuators placed in the vicinity of the tissues or by acoustic radiation force generated by an ultrasound probe.

In a non limiting embodiment, the elastography device 7 is adapted to measure physicals parameters of the liver from the group consisting of elasticity, viscosity, ultrasound attenuation, and shear wave speed, or any combination thereof.

In the example illustrated in FIG. 1, the non-invasive system 1 also comprises a second measurement slave device constructed and arranged to carry out measurements of physical parameters 8. The second physical measurement slave device 8 is for example an in-vivo body composition analyzer adapted to measure parameters from the group consisting of weight, body fat percentage, and body lean percentage, or any combination thereof.

In the example illustrated in FIG. 1, the non-invasive system 1 also comprises a slave device constructed and arranged to collect demographic and personal parameters 9, for instance, age, gender, height, weight. This slave device 9 may be a computer. The computer may include a memory or machine readable medium or be connected to a memory or a machine readable medium encoded with instructions to carry one or more operations.

The non-invasive system 1 comprises also a master device 10 constructed and arranged to collect the parameters measured and collected in order to calculate the accurate, reliable, standardized and complete score.

Therefore, according to the example illustrated in FIG. 1, the master device 10 is constructed and arranged to collect the parameters from:
  the first in-vitro measurement slave device 2 constructed and arranged to carry out measurements of biological parameters which is formed according to the example by a point of care testing of the type clinical chemistry analyzer,
  the second in-vitro measurement slave device 6 constructed and arranged to carry out measurements of biological parameters which is formed according to the example by a point of care testing of the type clinical hematology analyzer,
  the third in-vitro measurement slave device 12 constructed and arranged to carry out measurements of biological parameters (more particularly, genetic makers) which is formed according to the example by a DNA-based test analyzer,
  the fourth in-vitro measuremrnt slave device 13 constructed and arranged to carry out measurements of biological parameters (more particularly, immunologic markers) which is formed according to the example by a multiplexed magnetic assay,
  the first in-vivo measurement slave device constructed and arranged to carry out measurements of physical parameters which is formed according to the example by an elastography device 7 (a device with elastography modality),
  the second in-vivo measurement slave device 8 constructed and arranged to carry out measurements of physical parameters which is formed according to the example by a body composition analyzer,
  the slave device constructed and arranged to collect demographic and personal parameter 9 which is formed according to the example by a computer.

Therefore, the calculated score comprises biological, physical, personal and demographical parameters.

In the embodiment illustrated in FIG. 1, the master device is a server. The server may be physical (hardware) or virtual (as the cloud computing).

In a non limiting embodiment, the biological, physical, personal and demographical parameters are collected automatically by the master device 10. For that purpose, each measurement slave device 2, 6, 7, 8, 9, 12, 13 is connected to the master device 10 using, for instance, an infrared link, a wired connection, a wireless communication, or any form of data communication capable of transmitting and receiving information, or any combination thereof.

Furthermore, the master device 10 comprises a calculator 11 constructed and arranged to calculate the accurate, reliable, standardized and complete score.

In an embodiment, the master device is a computer. In this embodiment, the biological, physical, personal and demographical parameters may be collected via an interface, such as a keyboard, on which the user enters parameters measured by the slave devices. In this example, the master device comprises a display screen capable of displaying the calculated accurate, reliable, standardized and complete score.

Various forms of computer readable media may be involved in carrying one or more sequences of one or more instructions to processor of the master device 10 for execution. For example, the instructions may initially be borne on a magnetic disk of a remote computer. The remote computer can load the instructions into its dynamic memory and send the instructions over a telephone line using a modem. A modem local can receive the data on the telephone line and use an infrared transmitter to convert the data to an infrared signal. An infrared detector coupled to bus can receive the data carried in the infrared signal and place the data on bus. Bus carries the data to main memory, from which processor of the master device 10 retrieves and executes the instructions. The instructions received by main memory may optionally be stored on storage device either before or after execution by processor of the master device 10. A communication interface can be coupled to bus. Communication interface provides a two-way data communication coupling to a network link that is connected to a local network. For example, communication interface may be an integrated services digital network (ISDN) card or a modem to provide a data communication connection to a corresponding type of telephone line. As another example, communication interface may be a local area network (LAN) card to provide a data communication connection to a compatible LAN. Wireless links may also be implemented. In any such implementation, communication interface sends and receives electrical, electromagnetic or optical signals that carry digital data streams representing various types of information.

Network link typically provides data communication through one or more networks to other data devices. For example, network link may provide a connection through local network to the of the master device 10 operated by an Internet Service Provider (ISP). ISP in turn provides data communication services through the worldwide packet data communication network, now commonly referred to as the "Internet". Local network and Internet both use electrical, electromagnetic or optical signals that carry digital data streams. The signals through the various networks and the signals on network link and through communication interface, which carry the digital data, are exemplary forms of carrier waves transporting the information.

The master device 10 can send messages and receive data, including program code, through the network(s), network link, and communication interface. In the Internet example, a server might transmit a requested code for an application program through Internet, ISP, local network and communication interface. In accordance with the invention, one such downloaded application provides for the illumination optimization of the embodiment, for example. The received code may be executed by processor as it is received, and/or stored in storage device, or other non-volatile storage for later execution. In this manner, the master device 10 may obtain application code in the form of a carrier wave.

In another non limited embodiment depicted in FIG. 2, the non-invasive system 1 for calculating a human or animal accurate, reliable, standardized and complete score comprises:
- an in-vitro measurement slave device 2 constructed and arranged to carry out measurements of biological parameters formed by a point of care testing,
- a in-vivo measurement slave device constructed and arranged to carry out measurements of physical parameters formed by an elastography device 7 (for example, the elastography device is the FIBROSCAN® (an ultrasound apparatus for measuring the hardness and elasticity of tissues and organs), FIBROSCAN is a trademark registered),
- a master device 10 located in the first in-vitro measure slave device 2, the master device 10 being constructed and arranged to collect biological parameters from the point of care testing and physical parameter from the elastography device 7 and calculate the accurate, reliable, standardized and complete score.

In another non limiting embodiment depicted in FIG. 3, the non-invasive system 1 for calculating a human or animal accurate, reliable, standardized and complete score comprises:
- an in-vivo measurement slave device 7 constructed and arranged to carry out measurements of physical parameters formed by an elastography device,
- an in-vitro measurement slave device 2, located in the elastography device 7, constructed and arranged to carry out measurements of biological parameters formed by a point of care testing,
- a master device 10, located also in the elastography device 7, the master device 10 being constructed and arranged to collect biological, physical, personal and demographical parameters and calculate the score.

FIG. 4 illustrates an embodiment of the invention showing a non-invasive method 100 for calculating a human or animal score, the method 100 comprising:
- in the vicinity of a patient (in other words in the room where the measurements are carried out), measuring and calculating biological parameters 101;
- in the vicinity of a patient (in other words in the room where the measurements are carried out), measuring and calculating physical parameters 102;
- determining 103 the human or animal score comprising the biological and physical parameters that are measured and calculated. The step of determining 103 may be realized in the room where the measurements are carried out or at a remote room/location.

The embodiments of the invention have significant benefits:
- The accurate, reliable, standardized and complete score can be obtained shortly (even during the consultation),
- It is not necessary to qualify laboratories because the disposable device 4 is standard and the reagents are in it with all necessary control means,
- Better control of time between the blood sample taken from the body and measurements: no problem of transportation of blood samples,
- No problem due to manual entry measures (no conversion of units, no risk of incorrect entry),
- Possibility to combine the results of several devices, on site,
- Ability to correct the influence of certain parameters on the other: for example the influence of liver enzymes on liver stiffness.

According to an embodiment of the invention, the measurement slave devices and/or master device may each include one or more processors executing one or more sequences of one or more instructions contained in a memory to perform their intended functions (carry out measurements, collect information, send information, . . . ). In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to processor for execution. Such a medium may take many forms, including but not limited to, non-volatile media, volatile media, and transmission media. Non-volatile media include, for example, optical or magnetic disks, such as storage device. Volatile media include dynamic memory, such as main memory. Transmission media include coaxial cables, copper wire and fiber optics, including the wires that comprise bus. Transmission media can also take the form of acoustic or light waves, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor for execution. For example, the instructions may initially be borne on a magnetic disk of a remote computer. The remote computer can load the instructions into its dynamic memory and send the instructions over a telephone line using a modem.

It is to be understood that the present invention contemplates that, to the extent possible, one or more features of any embodiment can be combined with one or more features of any other embodiment.

The descriptions above are intended to be illustrative, not limiting. Thus, it will be apparent to one skilled in the art that modifications may be made to the invention as described without departing from the scope of the claims set out below.

The invention claimed is:

1. An elastography system for calculating a human or animal score, said elastography system comprising:
   a blood chemical analyzer configured to carry out measurements of one or more blood parameters of a patient;
   an elastography apparatus including an ultrasonic transducer configured to emit ultrasound shots and to receive corresponding echo signals to track how biological tissues of the patient are moved by a shear wave generated by the elastography apparatus, the elastography apparatus configured to carry out measurements of physical parameters of the patient, the physical parameters including at least elasticity and ultrasound attenuation associated with the biological tissues,
   wherein the blood chemical analyzer is directly operatively connected to the elastography apparatus, and
   wherein the elastography system is adapted to carry out the measurements of the one or more blood parameters and the measurements of the physical parameters concurrently or within a same time frame, and a master device configured to collect said one or more blood parameters and at least one of said physical parameters, the master device including a processor and a computer-readable medium having machine-executable instructions to, when executed by the processor, calculate said human or animal score on the basis of the measurements of the one or more blood parameters and the at least one of said physical parameters.

2. The elastography system according to claim 1, wherein the blood chemical analyzer configured to carry out measurements of one or more blood parameters is an in-vitro analyzer.

3. The elastography system according to claim 2, wherein the in-vitro analyzer is a DNA-based test analyzer.

4. The elastography system according to claim 3, wherein the DNA-based test analyzer is configured to measure genetic markers selected from the group consisting of: IL28, AZIN1, TLR4, TRPM5, and any combination thereof.

5. The elastography system according to claim 2, wherein the in-vitro analyzer is an immunology test analyzer.

6. The elastography system according to claim 5, wherein the immunology test analyzer is configured to measure genetic markers selected from the group consisting of: Albumin, Bilirubin, CRP, Ferritin, Alpha 2 macroglobulin, Hyaluronic acid, Laminin, Apolipoprotein A1, Haptoglobin, PIIINP, TIMP-1, MMPs, Adiponectin, IL-6, Alpha Fetoprotein, CK18, Chemokine ligand 2, TNF alpha, HbA1 c, anti-HCV, HBsAg, HBsAb, HbeAg, HbeAb, HbcAb and any combination thereof.

7. The elastography system according to claim 1, wherein the one or more blood parameters are selected from the group consisting of:
   albumin,
   alkaline phosphastase,
   aspartate aminotransferase,
   alanine aminotransferase,
   amylase,
   bilirubin,
   blood urea nitrogen,
   calcium,
   creatine kinase,
   chloride,
   creatinine,
   c-reactive protein,
   gamma glutamyl,
   transpeptidase,
   glucose,
   potassium,
   magnesium,
   sodium,
   phosphorus,
   total carbon dioxyde,
   total protein,
   uric acid,
   total cholesterol,
   high density lipoprotein,
   triglycerides,
   hyaluronic acid,
   alpha 2 macroglobulin, and any combination thereof.

8. The elastography system according to claim 7, wherein the one or more blood parameters are selected from the group consisting of: aspartate aminotransferase, hyaluronic acid, alanine aminotransferase, bilirubin, alpha 2 macroglobulin, gamma glutamyl, transpeptidase, and any combination thereof.

9. The elastography system according to claim 1, wherein the one or more blood parameters are hematology parameters selected from the group consisting of:
   platelet,
   white blood cell,
   red blood cell,
   prothrombin index, and
   INR, and any
   combination thereof.

10. The elastography system according to claim 1, wherein the one or more blood parameters are selected from the group consisting of:
   platelet,
   prothrombin index, and
   INR, and any
   combination thereof.

11. The elastography system according to claim 1, wherein the elastography apparatus is configured to measure parameters of the liver including elasticity and ultrasound attenuation and at least one parameter selected from the group consisting of:
   stiffness,
   viscosity,
   shear wave speed, and any combination thereof.

12. The elestography system according to claim 1, wherein the master device is configured to collect personal and demographical parameters.

13. The elastography system according to claim 1, wherein the one or more blood parameters include liver enzymes.

14. The elastography system according to claim 1, wherein the blood chemical analyzer is directly operatively connected to the elastography apparatus by a wired connection, an infrared link or a wireless link.

15. The elastography system according to claim 1, wherein the computer-readable medium of the master device includes machine-executable instructions to, when executed by the processor, automatically collect said one or more blood parameters and at least one of said physical parameters.

16. The elastography system according to claim 1, wherein the computer-readable medium of the master device includes machine-executable instructions to, when executed by the processor, carry out the measurements of said one or more blood parameters via the blood chemical analyzer and of said at least one of said physical parameters via the elastography apparatus.

\* \* \* \* \*